US010646657B2

(12) United States Patent
Dowds

(10) Patent No.: US 10,646,657 B2
(45) Date of Patent: *May 12, 2020

(54) EXTENDED FINGER FLANGE FOR SYRINGE SYSTEMS

(71) Applicant: SAFETY SYRINGES, INC., Carlsbad, CA (US)

(72) Inventor: Philip E. Dowds, San Diego, CA (US)

(73) Assignee: SAFETY SYRINGES, INC., Carlsbad, CA (US)

(*) Notice: Subject to any disclaimer, the term of this patent is extended or adjusted under 35 U.S.C. 154(b) by 109 days.

This patent is subject to a terminal disclaimer.

(21) Appl. No.: 15/703,845

(22) Filed: Sep. 13, 2017

(65) Prior Publication Data

US 2018/0126084 A1 May 10, 2018

Related U.S. Application Data

(63) Continuation of application No. 15/182,363, filed on Jun. 14, 2016, now Pat. No. 9,802,000, which is a continuation of application No. 14/560,722, filed on Dec. 4, 2014, now Pat. No. 9,387,292, which is a continuation of application No. 13/096,663, filed on Apr. 28, 2011, now Pat. No. 8,920,385.

(60) Provisional application No. 61/331,752, filed on May 5, 2010.

(51) Int. Cl.
*A61M 5/31* (2006.01)
*A61M 5/32* (2006.01)

(52) U.S. Cl.
CPC ........ *A61M 5/3137* (2013.01); *A61M 5/3202* (2013.01); *A61M 5/3213* (2013.01); *A61M 5/3243* (2013.01); *A61M 2005/3139* (2013.01); *A61M 2005/3142* (2013.01)

(58) Field of Classification Search
CPC .............. A61M 5/3137; A61M 5/3202; A61M 5/3213; A61M 5/3243; A61M 2005/3139
USPC .................................................. 604/198, 227
See application file for complete search history.

(56) References Cited

U.S. PATENT DOCUMENTS

| 1,678,991 | A | 7/1928 | Marschalek |
| 5,472,430 | A | 12/1995 | Vaillancourt et al. |
| 5,607,399 | A | 3/1997 | Grimard et al. |
| 5,667,495 | A | 9/1997 | Bitdinger et al. |
| 5,672,161 | A | 9/1997 | Allen et al. |
| 5,700,247 | A | 12/1997 | Grimard et al. |
| D419,671 | S | 1/2000 | Jansen |
| 6,030,366 | A | 2/2000 | Mitchell |

(Continued)

FOREIGN PATENT DOCUMENTS

| EP | 0649318 B1 | 3/1999 |
| EP | 0882467 B1 | 10/2003 |

(Continued)

OTHER PUBLICATIONS

WO, PCT/US2011/035066—ISR and Written Opinion, dated Aug. 18, 2011.

*Primary Examiner* — Phillip A Gray
(74) *Attorney, Agent, or Firm* — One LLP

(57) ABSTRACT

The present disclosure describes an extended finger flange that facilitate use of syringe systems. The extended finger flange increases the surface area available for an end user's fingers thereby allowing a more secure grip on the device and providing greater control during administrations of the medication.

20 Claims, 5 Drawing Sheets

(56) References Cited

U.S. PATENT DOCUMENTS

| | | |
|---|---|---|
| 6,090,077 A | 7/2000 | Shaw |
| 6,171,283 B1 | 1/2001 | Perez et al. |
| 6,193,696 B1 | 2/2001 | Jansen et al. |
| 6,296,625 B1 | 10/2001 | Vetter et al. |
| 6,319,233 B1 | 11/2001 | Jansen et al. |
| 6,344,032 B1 * | 2/2002 | Perez ............... A61M 5/3271 604/110 |
| 6,599,272 B1 | 7/2003 | Hjertman et al. |
| 6,656,164 B1 | 12/2003 | Smith |
| 6,776,777 B2 | 8/2004 | Barrelle |
| 6,926,700 B2 | 8/2005 | Bressler et al. |
| 6,997,901 B2 | 2/2006 | Popovsky |
| 7,041,085 B2 | 5/2006 | Perez et al. |
| 7,101,355 B2 | 9/2006 | Doyle |
| 7,118,552 B2 | 10/2006 | Shaw et al. |
| 7,468,054 B2 | 12/2008 | Crawford et al. |
| 7,635,356 B2 | 12/2009 | Stamp |
| 7,678,086 B2 | 3/2010 | Chevallier |
| 7,850,661 B2 | 12/2010 | Chevallier et al. |
| 8,075,535 B2 | 12/2011 | Carrel et al. |
| 8,118,787 B2 | 2/2012 | Chevallier et al. |
| 8,298,193 B2 | 10/2012 | Field et al. |
| 8,496,627 B2 | 7/2013 | Chelak et al. |
| 8,771,235 B2 | 7/2014 | Chevallier et al. |
| 8,888,742 B2 | 11/2014 | Harms et al. |
| 8,945,065 B2 | 2/2015 | Torris et al. |
| 8,979,794 B2 | 3/2015 | Chevallier |
| 9,011,389 B2 | 4/2015 | Peruzzo et al. |
| 9,022,990 B2 | 5/2015 | Chevallier et al. |
| 9,050,416 B2 | 6/2015 | Feret et al. |
| 2003/0229316 A1 | 12/2003 | Hwang et al. |
| 2004/0167476 A1 * | 8/2004 | Westbye ............. A61M 5/3271 604/192 |
| 2004/0236281 A1 | 11/2004 | Popovsky |
| 2004/0236284 A1 | 11/2004 | Hoste et al. |
| 2005/0096597 A1 | 5/2005 | Crawford et al. |
| 2005/0159706 A1 | 7/2005 | Wilkinson |
| 2005/0159709 A1 | 7/2005 | Wilkinson et al. |
| 2007/0179441 A1 | 8/2007 | Chevallier |
| 2009/0036839 A1 | 2/2009 | Phalen |
| 2009/0270814 A1 | 10/2009 | Masi et al. |
| 2010/0217205 A1 | 8/2010 | Chevallier et al. |
| 2011/0118701 A1 | 5/2011 | Baney et al. |
| 2012/0232492 A1 | 9/2012 | Hato |
| 2012/0238962 A1 | 9/2012 | Chin et al. |
| 2013/0110051 A1 | 5/2013 | Ruan |
| 2014/0088512 A1 | 3/2014 | Quinn |
| 2014/0107577 A1 | 4/2014 | Boyd et al. |

FOREIGN PATENT DOCUMENTS

| | | |
|---|---|---|
| EP | 1381414 B1 | 9/2005 |
| EP | 1558310 B1 | 6/2008 |
| EP | 2623145 A1 | 8/2013 |
| WO | WO 02/070055 A1 | 9/2002 |
| WO | WO 2004/060445 A2 | 7/2004 |

* cited by examiner

EXTENDED FINGER FLANGE FOR SYRINGE SYSTEMS

CROSS-REFERENCE TO RELATED APPLICATIONS

This application is a continuation of U.S. application Ser. No. 15/182,363 filed Jun. 14, 2016, which is a continuation of U.S. application Ser. No. 14/560,722 filed Dec. 4, 2014, now U.S. Pat. No. 9,387,292, which is a continuation of U.S. application Ser. No. 13/096,663 filed Apr. 28, 2011, now U.S. Pat. No. 8,920,385, which claims the benefit of U.S. Provisional Application No. 61/331,752 filed May 5, 2010, all of which are incorporated by reference herein.

FIELD

The embodiments provided herein relate generally to syringe systems for administering therapeutic agents to patients. More specifically, the embodiments relate to an extended finger flange that can be coupled to a syringe system to facilitate use.

BACKGROUND

Because of the risk of communicable diseases, a number of syringes and adapters have been developed that are intended to prevent accidental needle sticks and/or inadvertent reuse of a syringe. The syringe safety systems come in a variety of forms. One form of a syringe safety system uses a needle guard comprising a body and an extendable shield. The shield can be manually or passively transitioned from a first, retracted position to a second, extended position following administration of the medicine within the syringe. In the extended position, the shield covers the needle, thereby protecting the user from accidental needle sticks.

In use, the syringe system is typically held by a user with two or more fingers engaging a finger grip of the syringe system and the user's thumb disposed on a thumb pad or top surface of the syringe's plunger. In many present systems, the finger grip area is quite small resulting in a device that may be difficult to manipulate and control, especially for end users with joint pain or limited dexterity.

Accordingly, an improved finger grip area for use with safety syringe systems would be useful.

SUMMARY

The embodiments presented herein are directed to an extended finger flange that can be coupled with a safety syringe system to facilitate the use of the syringe. The finger flange comprises lateral surfaces which increase the surface area available for the end user's fingers. The extended area makes it easier for the end user to grip the device and administer an injection.

The extended finger flange is a component that can be removably coupled with the syringe or syringe safety system. The extended finger flange can be press fit into place and/or it may include snap features which mate with one or more features on the syringe or syringe system to secure the extended finger flange into the desired location.

DESCRIPTION OF THE DRAWINGS

The details of the example embodiments, including structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

DETAILED DESCRIPTION

Figure 1:
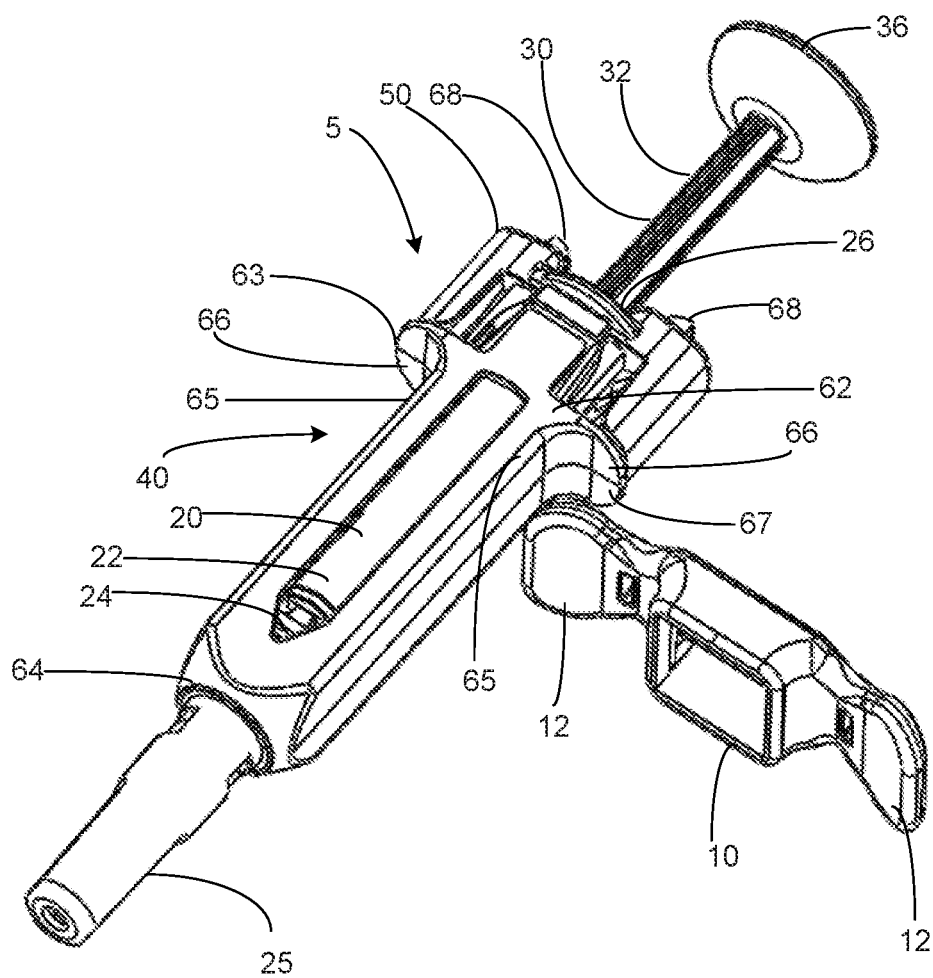
FIG. 1 shows an unassembled version of an exemplary embodiment of the present disclosure having a syringe system and a extended finger flange.

Turning to the figures, FIG. 1 depicts an exemplary embodiment of a syringe system 5 that can be used with the extended finger flange 10 of the present disclosure. As depicted, the syringe systems 5 includes a needle guard 40 configured to receive a syringe 20 having a plunger 30. The syringe 20 has a substantially smooth-walled cylindrical barrel 22, a hub or distal end 24 that is the administration end, and a proximal end 26. The proximal end 26 of the barrel 22 is configured to receive the plunger 30. The plunger 30 comprises a stem 32 and a radial portion or thumb pad 36. The distal end 24 of the cylindrical barrel 22 preferably comprises a needle port or luer fitting. Preferably, the needle of the syringe 20 is covered with a cap 25 prior to the attachment of the extended finger flange and/or administration of the medication.

The syringe 20 is preferably housed inside the needle guard 40. Although the extended finger flange 10 of the present disclosure may be used with a variety of needle guards or directly with a syringe, in an exemplary embodiment the needle guard 40 comprises a body 50 for receiving and holding the syringe 20 and a shield 60 slidably attached to the body 50.

In one exemplary embodiment, the shield 60 is a tubular member adapted to slidably fit on the body 50 and has a proximal end 62 and a distal end 64. The shield 60 comprises a pair of finger flanges 66. The distal surfaces 67 of the finger flanges 66 typically provide only a small surface area for the end user's fingers to grip and secure the syringe system.

The shield 60 can include one or more trigger fingers 68 that extend proximally from the proximal end 62 of the shield 60. During administration of the medication, the radial portion 36 of the plunger 30 contacts the trigger fingers 68. This action allows the shield 60 to transition from a first, retracted position to a second, extended position to cover the needle. The needle guard 40 can also include a spring mechanism coupled to the body 50 and the shield 60 for biasing the shield 60 towards an extended position when the trigger fingers 68 are deflected radially.

In an exemplary embodiment, the extended finger flange device 10 fits onto the needle guard 40 of the syringe system 5. The lateral flaps 12 of the extended finger flange 10 increase the surface area and make it easier for the end user to grip the device and administer an injection. The addition of the extended finger flange 10 makes it easier for end users that have joint pain or limited dexterity to handle and grip the device when they self-administer an injection by extending the area that they have to grip.

Figure 2:
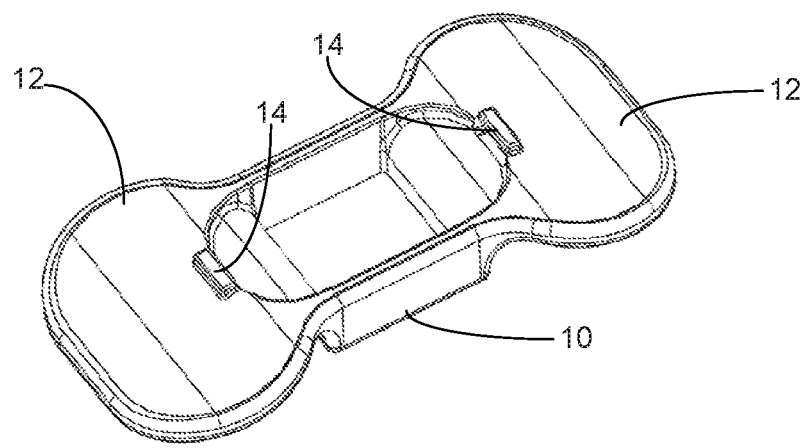
FIG. 2 shows an exemplary embodiment of the extended finger flange of the present disclosure.
Figure 4:
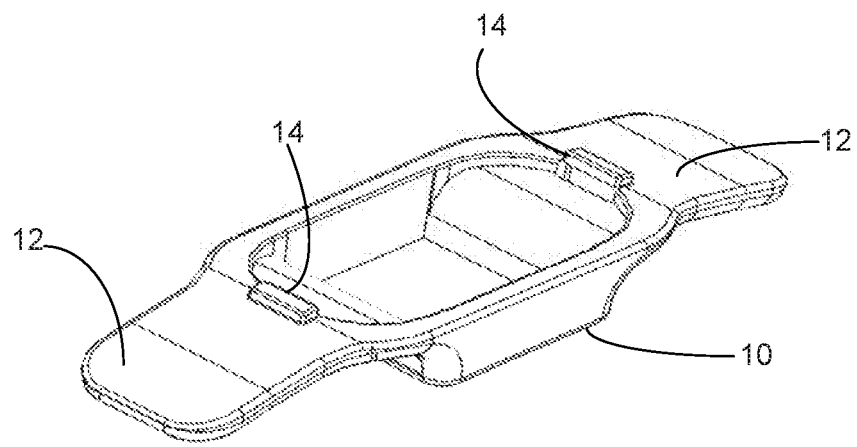
FIG. 4 shows another exemplary embodiment of the extended finger flange of the present disclosure.
Figure 3:
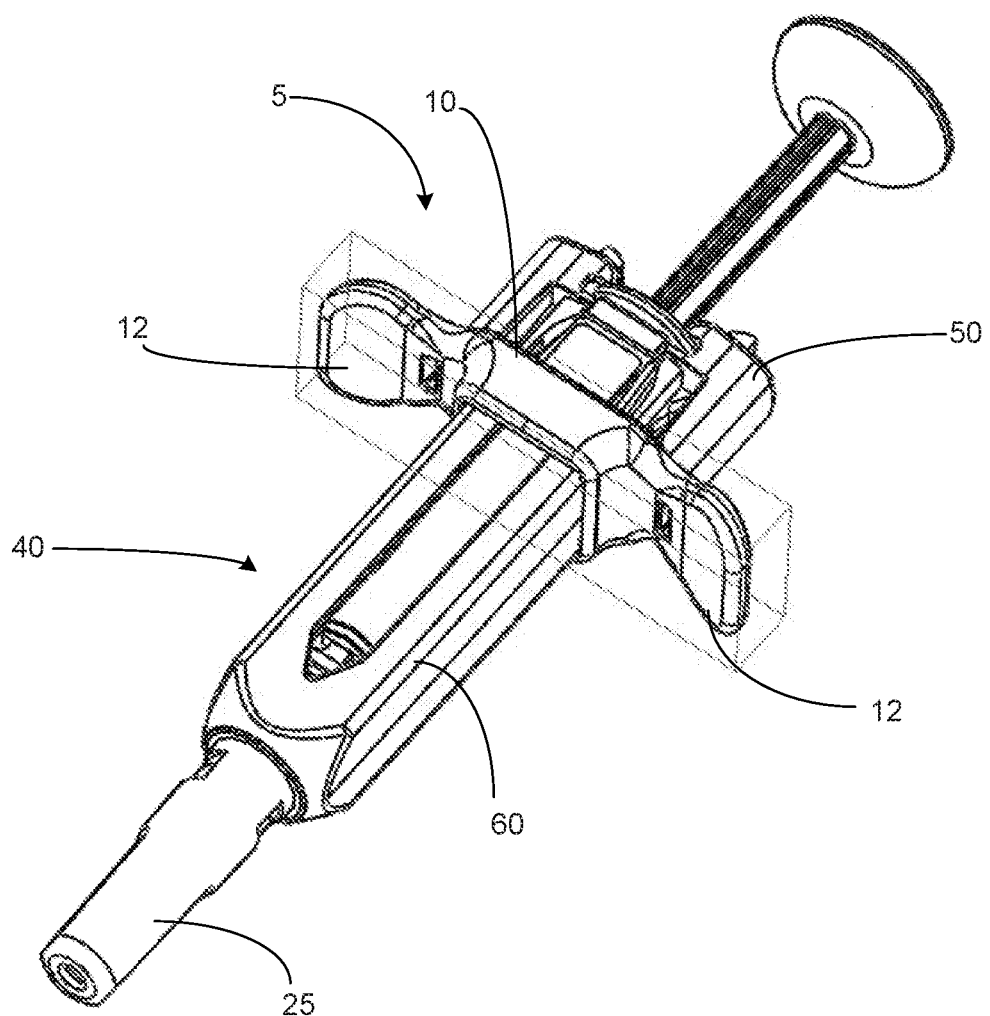
FIG. 3 shows an exemplary embodiment wherein the extended finger flange is attached to the syringe system.

The exact dimensions, orientation, and configuration of the lateral flaps 12 of the extended finger flange 10 can be varied to fit the requirements of the patient population served by the drug medication. For example, as shown in FIG. 2, the lateral flaps 12 can comprise a wide, rounded area or the lateral flaps 12 can comprise a more rectangular shape as shown in FIG. 4. As another example, as shown in FIG. 3, the finger flaps 12 can have a downward orientation to further assist the end user in holding the device. The extended finger flange 10 is generally molded from plastic, such as, polypropylene, k-resin, or polycarbonate, or the like. Alternatively, the extended finger flange 10 can be manufactured using an over molded process (FIG. 4). In this embodiment, a soft durometer elastomare could be molded over a ridged core to provide support to the device and a soft spongy feel to the user that would give a better grip and reduce the pressure on the user's fingers.

As shown in FIG. 3, the extended finger flange 10 is placed onto the outside of the needle guard 40 of the syringe system 5. The extended finger flange 10 can be coupled with the syringe system 5 in a variety of ways. As one example, the extended finger flange 10 can be coupled to the syringe system 5 using a slight press fit over the needle guard 40. In another embodiment, the extended finger flange 10 can be coupled to the syringe system 5 through a positive snap feature 14 (FIG. 2) that couples the extended finger flange 10 and the syringe system 5 together. In this embodiment, the extended finger flange 10 comprises one or more snap features 14 that are configured to engage complimentary portions of the shield 60 of the needle guard 40. For example, the snap features 14 on the extended finger flange 10 can be configured to engage the lateral ends 63 (FIG. 1) of the finger flange 66 on the shield 60.

Figure 5:
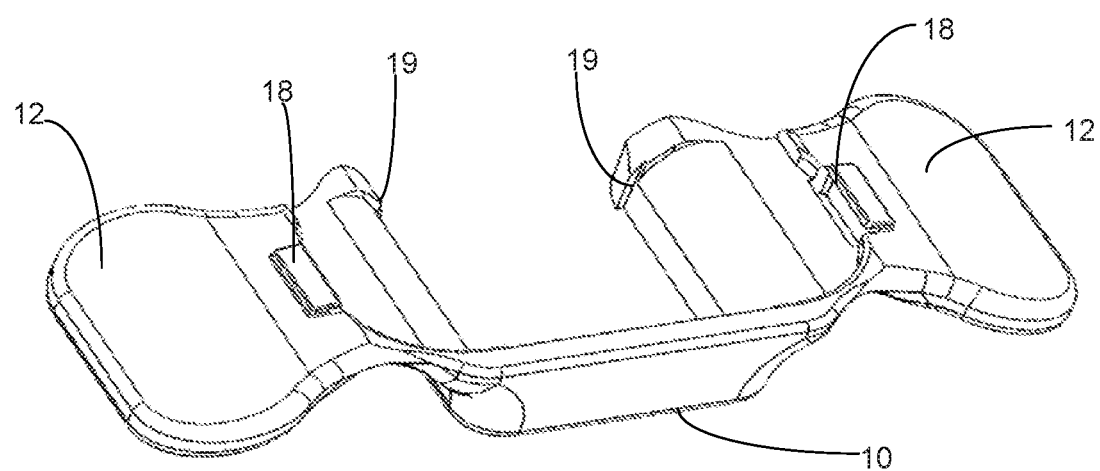
FIG. 5 shows another exemplary embodiment of the extended finger flange of the present disclosure.

In an alternative embodiment shown in FIG. 5, the extended finger flange 10 can be configured to slide on to the safety system 5 from the side. In this embodiment, the central portion of the extended finger flange 10 comprises a "C" shape. Attaching the extended finger flange 10 from the side reduces the chance of damaging the needle when attaching the extended finger flange 10 to the syringe system 5. In this embodiment, the extended finger flange 10 can be held in place by, for example, two upper snap features 18 and two side snap features 19. The snap features 18, 19 can engage complimentary portions of the shield 60. For example, the side snap features 19 can interact with recesses 65 on the shield 60, and the upper snap features 18 can interact with the lateral ends 63 of the finger flange 66 of the shield 60.

Figure 6:
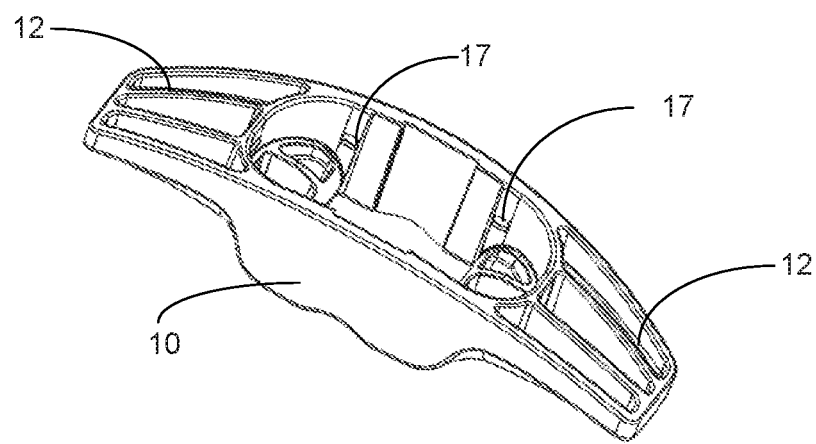
FIG. 6 shows another exemplary embodiment of the extended finger flange of the present disclosure.
Figure 7A:
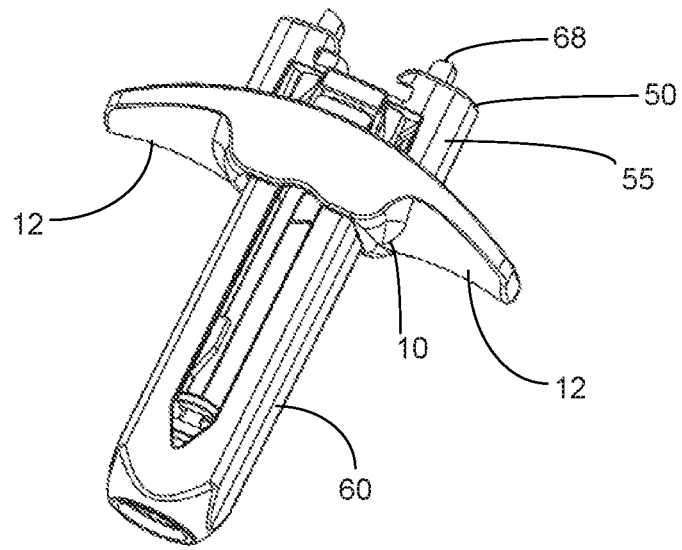
FIG. 7A shows the embodiment of the extended finger flange of FIG. 6 viewed from an orientation in which the underside of the extended finger flange is visible, wherein the extended finger flange is attached to an exemplary needle guard.
Figure 7B:
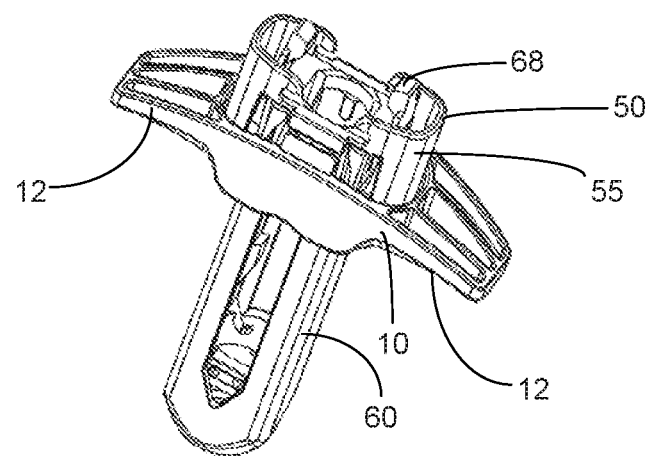
FIG. 7B shows the embodiment of the extended finger flange of FIG. 6 viewed from an orientation in which the top of the extended finger flange is visible, wherein the extended finger flange is attached to an exemplary needle guard.

In yet another exemplary embodiment, as shown in FIG. 6, the extended finger flange 10 comprises one or more internal snaps 17 that press fit against the finger flange 66 of the shield 60 when the extended finger flange 10 is fully inserted onto the needle guard 40. Once fully inserted (see FIGS. 7A and 7B), the snap features 17 press against the lateral edges of the finger flange 66 but not against the lateral ends 63 and, thus, does not apply pressure against the sidewall of the device. This configuration prevents the extended finger flange 10 from deforming the needle guard 40. Such deformation could cause an increase in friction between the shield 60 and body 50 of the needle guard 40 and possibly prevent the shield 60 from extending relative to the body when activated.

While the invention is susceptible to various modifications, and alternative forms, specific examples thereof have been shown in the drawings and herein described in detail. It should be understood, however, that the invention is not to be limited to the particular forms or methods disclosed, but to the contrary, the intention is to cover all modifications, equivalents, and alternatives falling within the spirit and scope of the appended claims.

The invention claimed is:

1. A syringe system comprising
a needle guard having a shield and a body, the body being configured to receive a syringe, the needle guard having a pair of finger flanges integral to one of the shield and the body and extending laterally adjacent a proximal end of one of the shield and the body; and
an extended finger flange separate from the pair of finger flanges integral to one of the shield and the body and removably coupled with the needle guard, wherein the extended finger flange comprises a central portion configured to receive the needle guard and an extended area that increases the surface area available for a user's fingers to grip beyond the surface area of the pair of finger flanges integral to one of the shield and the body of the needle guard, wherein the extended finger flange comprises one or more latching features releasably latchable to a complimentary portion of the needle guard.

2. The syringe system of claim 1, wherein the one or more latching features comprise one or more snap features internally positioned within the central portion of the extended finger flange.

3. The syringe system of claim 1, wherein the snap features of the extended finger flange engage a recess on the needle guard.

4. The syringe system of claim 1, wherein the extended finger flange is removably coupled to the needle guard through a press fit.

5. The syringe system of claim 1, wherein the extended finger flange further includes a lateral opening in communication with the central portion and configured to enable mounting of the extended finger flange onto the needle guard in a lateral direction with respect to a longitudinal axis of the needle guard.

6. The syringe system of claim 1, wherein the extended finger flange comprises a soft durometer elastomer molded over a rigid core.

7. The system of claim 1, wherein the shield comprises one or more trigger fingers extending proximally from a proximal end of the shield, wherein the shield is biased toward an extended position when the trigger fingers are deflected radially such that the shield covers a needle of the syringe during and after administration of medication.

8. The system of claim 7, wherein the needle guard comprises a spring mechanism coupled to the body and the shield, the spring mechanism configured for biasing the shield toward the extended position.

9. An extended finger flange for a syringe system, the syringe system comprising a syringe and a needle guard operably coupled to the syringe, the needle guard including a shield and a body and a pair of finger flanges integral to one of the shield and the body and extending laterally adjacent a proximal end of one of the shield and the body, the extended finger flange comprising:
- a central attachment area configured to receive a needle guard of a syringe system, and
- an extended area extending from the central attachment area and configured to be engaged by an end user's fingers, the extended area increasing the surface area available for the end user's fingers to engage beyond the surface area of the pair of finger flanges integral to one of the shield and the body of the needle guard of the syringe system, wherein the extended finger flange comprises one or more latching features releasably latchable to a complimentary portion of the needle guard.

10. The extended finger flange of claim 9, wherein the central attachment area is dimensioned relative to the syringe system such that the extended finger flange is press fit into place.

11. The extended finger flange of claim 9, wherein the one or more latching features comprise one or more snap features internally positioned within the central portion of the extended finger flange.

12. The extended finger flange of claim 9, wherein the snap features of the extended finger flange engage a recess on the needle guard.

13. The extended finger flange of claim 9, wherein the extended finger flange is removably coupled to the needle guard through a press fit.

14. The extended finger flange of claim 9, wherein the extended finger flange further includes a lateral opening in communication with the central portion and configured to enable mounting of the extended finger flange onto the needle guard in a lateral direction with respect to a longitudinal axis of the needle guard.

15. The extended finger flange of claim 9, wherein the extended finger flange comprises a soft durometer elastomer molded over a rigid core.

16. The system of claim 9, wherein the shield comprises one or more trigger fingers extending proximally from a proximal end of the shield, wherein the shield is biased toward an extended position when the trigger fingers are deflected radially such that the shield covers a needle of the syringe during and after administration of medication.

17. The system of claim 16, wherein the needle guard comprises a spring mechanism coupled to the body and the shield, the spring mechanism configured for biasing the shield toward the extended position.

18. A syringe system comprising
- a needle guard having a shield and a body, the body being configured to receive a syringe, the needle guard having a figure grip surface area integral to one of the shield and the body; and
- an extended finger flange separate from the figure grip surface area integral to one of the shield and the body and removably coupled with the needle guard, wherein the extended finger flange comprises a central portion configured to receive the needle guard and an extended area having a that increases the surface area available for a user's fingers to grip beyond the surface area available for the user's fingers to grip on the needle guard on the figure grip surface area integral to one of the shield and the body, wherein the extended finger flange comprises one or more latching features releasably latchable to a complimentary portion of the needle guard.

19. The syringe system of claim 18, wherein the one or more latching features comprise one or more snap features internally positioned within the central portion of the extended finger flange.

20. The syringe system of claim 18, wherein the extended finger flange is removably coupled to the needle guard through a press fit.

* * * * *